United States Patent [19]

Miyatake et al.

[11] Patent Number: 4,808,825
[45] Date of Patent: Feb. 28, 1989

[54] FLUID ANALYZER

[75] Inventors: Kimio Miyatake; Takao Imaki; Masahiko Fujiwara, all of Kyoto, Japan

[73] Assignee: Horiba, Ltd., Kyoto, Japan

[21] Appl. No.: 946,183

[22] Filed: Dec. 22, 1986

[30] Foreign Application Priority Data

Dec. 23, 1985 [JP] Japan .................. 60-290258

[51] Int. Cl.$^4$ .................. G01J 1/00; G01N 21/00
[52] U.S. Cl. ................. 250/343; 356/437
[58] Field of Search ............. 250/343, 373; 356/436, 356/437, 440

[56] References Cited

U.S. PATENT DOCUMENTS 3,562,524 2/1971 Moore et al. ............ 250/343
3,946,239 3/1976 Salzman et al. .......... 250/461.2
4,557,603 12/1985 Oehler et al. ........... 250/343
4,662,755 5/1987 Aoki et al. ............. 250/343

Primary Examiner—Janice A. Howell
Attorney, Agent, or Firm—Wenderoth, Lind & Ponack

[57] ABSTRACT

A fluid analyzer having a light source, a cell for receiving fluid to be analyzed and reference fluid and positioned to receive light from the light source, a detector positioned for receiving the output from the cell, and a light source body having inner reflective walls with a curved profile in the direction extending between the light source and the cell for forming a first focal point at one end thereof and a second focal point at the other end thereof. The light source is positioned in the light source body substantially coincident with the first focal point, and the other end of the light source body extends around the end of the cell which is toward the light source and with the second focal point within the cell.

5 Claims, 2 Drawing Sheets

FLUID ANALYZER

The present invention relates to a fluid analyzer for analyzing a fluid and consisting of a light source, a cell, a detector and the like.

BACKGROUND OF THE INVENTION AND PRIOR ART

In general, an analyzer such as an infrared gas analyzer, the larger the quantity of light incident upon a cell from a light source, the higher the detecting sensitivity and the more highly accurate the measurement which is achieved.

Although in general a heating resistor has been used as a light source for such an analyzer, such a light source must not be a so-called point light source because of the resistance generated heat therefrom and the limited useful life. Thus, such a light source has a definite size, which results in the disadvantage that the light from such a light source is scattered, and the quantity of light incident upon the cell is reduced.

Consequently, in a conventional analyzer, as shown in FIG. 5, where a pneumatic detector having a relatively large light-receiving surface is used as a detector 50, the detecting sensitivity has been increased by making the light from a light source 51 incident upon a cell 52 in a manner such that it is confined within a predetermined width. As shown in FIG. 6, where a solid detector having a relatively small light-receiving surface is used as a detector 60, the detecting sensitivity has been increased by collecting the light from a light source 61 by means of a lens 62 having superior permeability to infrared rays, and directing this collected light onto a cell 63. Alternatively, the quantity of light incident upon the cell can be increased by using a laser light source as the light source 61.

In said FIGS. 5 and 6, reference numerals 53 and 54 and 64 and 65 designate electro-magnetic valves provided in reference-gas supply means 55 and 66 and sample-gas supply means 56 and 67, respectively. Reference numerals 57 and 68 designate controllers for controlling the opening and closing of these electro-magnetic valves 53, 54, 64 and 65. Preamplifiers 58 and 69 amplify the output of detectors 50 and 60, respectively.

In the above described prior art analyzer as shown in FIG. 5, since a cell 52 having a large cross-sectional area corresponding to the size of the light-receiving surface of the detector 50 must be used, the volume of the cell 52 is large, in particular in the case of a fluid modulation type gas analyzer as shown in FIG. 5, and a disadvantage has occurred in that the analyzer requires a large amount of gas and is expensive.

In addition, in the analyzer as shown in FIG. 6, a disadvantage has occurred in that it is expensive due to a use of the lens 62 or the laser light source.

OBJECTS AND BRIEF SUMMARY OF THE INVENTION

The present invention has as its objects to overcome the above described problems and to provide an inexpensive analyzer having a high detecting accuracy.

In order to achieve the above described objects, the analyzer according to the present invention has a light source body having a curved inner reflecting surface with a light source of a focal point at one end and having one end of the gas cell within the other end of said body.

The light source body has the cross-sectional shape of an ellipse or a combination of two hyperbolic lines or a combination of two parabolas, or the like, so as to produce a focal point at both ends. It is not always necessary to position the light source and the one end of the cell exactly on the focal points of said light source body. They may be positioned in the vicinity of said focal points while still obtaining a good effect.

By means of the above described construction, scattered light from the light source at one focal point of the light source body is reflected by the inside circumferential surface of the light source body to the cell provided at the other focal point. Accordingly, said reflected light is incident upon the cell in addition to the light which has come directly to the cell from the light source without being scattered after radiating from the light source, so that the quantity of light incident upon the cell is greatly increased, whereby the detecting sensitivity can be improved and a highly accurate measurement can be achieved.

BRIEF DESCRIPTION OF THE DRAWINGS

The preferred embodiments of the present invention will now be described with reference to the drawings, in which.

DETAILED DESCRIPTION OF THE INVENTION

Figure 1:
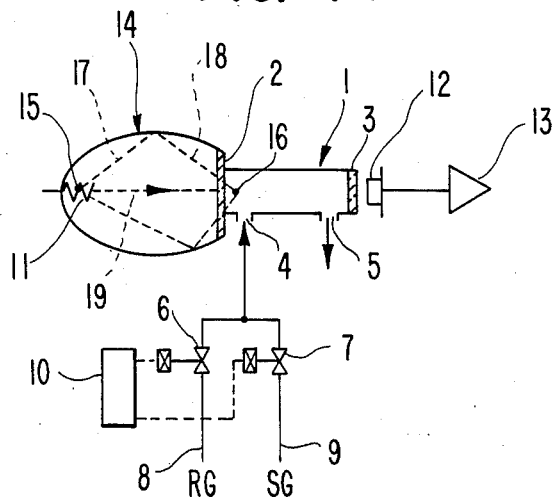
FIG. 1 is a schematic cross-sectional view of a so-called single cell type infrared fluid analyzer to which the present invention is applied.

Referring to FIG. 1, reference numeral 1 designates a cell, the opposite end portions of which are tightly closed by cell windows 2 and 3 of radiation transparent material, such as light transparent material. Reference numeral 4 designates a fluid inlet port, and reference numeral 5 designates a fluid outlet port. While the specific fluid can be gas or liquid, the embodiments disclosed are specifically for gas. It will be understood that the principles can be applied to liquid analyzers.

Electro-magnetic valves 6 and 7 are provided in a reference-gas supply means 8 and a sample-gas supply means 9, respectively, and the opening and closing of valves 6 and 7 are controlled by a control signal from a controller 10 so that a desired amount of a reference gas RG and a sample gas SG may be alternately supplied to said cell 1 in a predetermined desired cycle.

A light source 11 is positioned opposite one cell window 2, and a detector is positioned opposite to the other cell window 3. The detector can be, for example, a solid detector. A pneumatic detector can also be used. A preamplifier 13 amplifies the signal from the detector 12.

Figure 7:
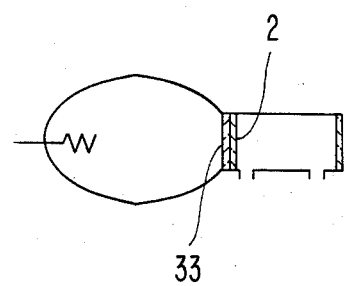
FIG. 7 is a view of a modified form of the analyzer of FIG. 1.

A light source body 14 is provided which is hollow and which has an oval longitudinal cross-section and a mirror-finished inside circumferential surface. The light source 11 is positioned within one end thereof and the other end is closed by the cell window 2. The cell window 2 also serves as the window of the light source body. Alternatively, the body can have a separate window 33 which abuts the window 2, as shown in FIG. 7. The oval cross-sectional surface of the body 14 has a shape for forming a first focal point 15 at one end with which the light source 11 is substantially coincident and a second focal point 16 positioned just inside the cell window 2 within the cell 1.

In the analyzer constructed in the above described manner, since the light source 11 is positioned coincident with one focal point 15 of the light source body 14, scattered light 17 radiated from this light source 11 is reflected by the inside circumferential surface of the body 14 and reflected light 18 is directed to the other focal point 16 so as to be incident upon the gas in cell 1. Thus, since said reflected light 18 is incident upon the gas in cell 1 in addition to a light 19 directly incident upon the cell 1 from the light source 11, (hereinafter referred to as a direct incident light) the quantity of light incident upon said cell 1 is greatly increased and the detecting sensitivity is increased sufficiently that highly accurate measurement can be achieved.

Figure 6:
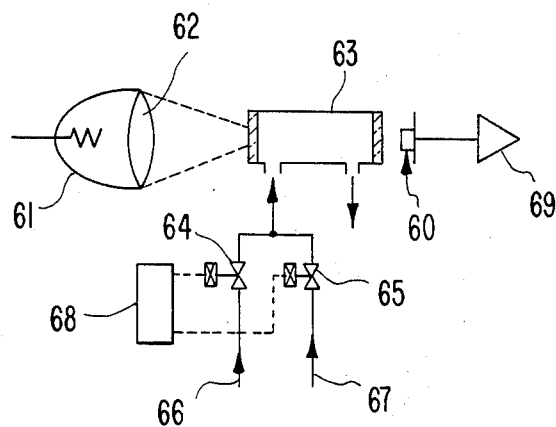

According to experiments made by the inventors, the output of an analyzer having the above described construction was about 1.5 times that of a conventional analyzer as shown in FIG. 6.

As will be understood from the foregoing description, light radiated from the light source 11 can be caused to be incident upon the cell 1 very efficiently by providing the light source body 14, having the necessary longitudinal cross-sectional shape to produce the two focal points, positioning the light source 11 at one focal point 15 of the light source body 14, and positioning the one end of the cell 1 at the other focal 16.

Figure 2:
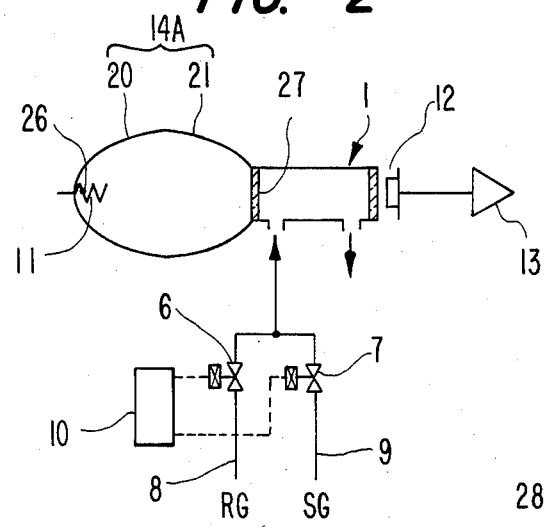
FIG. 2 is a similar view of an analyzer having a different shape light source body.
Figure 3:
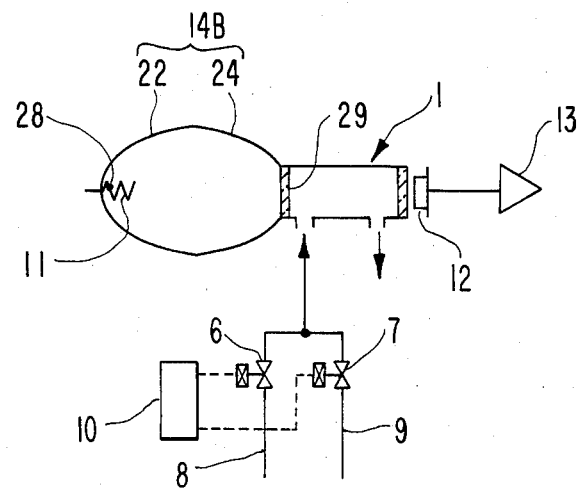
FIG. 3 is a similar view of an analyzer having a further different shape light source body.

The light source body 14 may have many different shapes. For example, the longitudinal cross-sectional shape of the inner surface of the body may be a combination of two curves 20 and 21 connected at the open sides thereof to form body 14A having focal points 26 and 27, for example two hyperbolic curves, or a hyperbolic curve and a parabola, as shown in FIG. 2, or a combination of two parabolas 22 and 24 connected at the open sides thereof to form the body 14B having focal points 28 and 29 as shown in FIG. 3. Said hyperbolic curves 20 and 21 need not always be the same shape and said parabolas 22 and 24 need not always be the same shape.

Figure 4:
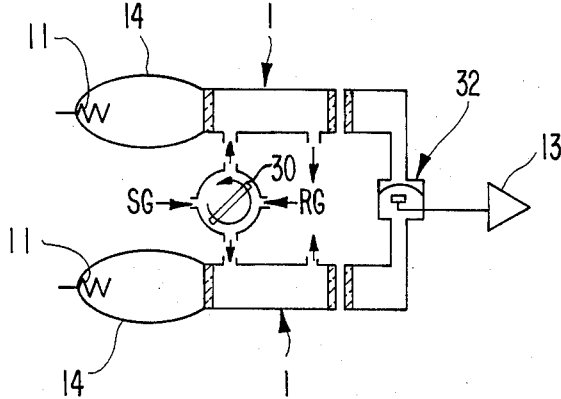
FIG. 4 is a similar view of a double cell type analyzer.
Figure 5:
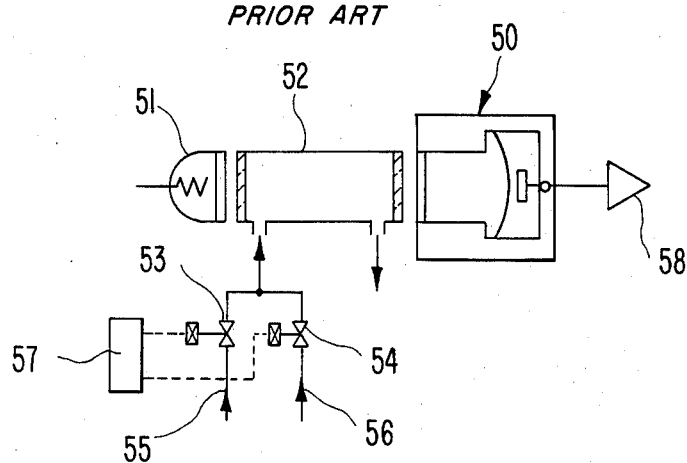
FIGS. 5 and 6 are similar views of prior art analyzers.

FIG. 4 shows the use of a light source body 14 as shown in FIG. 1 in a double-cell type analyzer. Referring to FIG. 4, reference numeral 30 designates a gas supply changing-over valve for changing over the supply of reference gas RG and sample gas SG to respective cells 1, reference numeral 32 designating a pneumatic type detector.

The present invention is not limited to the above described preferred embodiments. It goes without saying that the present invention can also be applied to an analyzer in which an output modulation is carried out by means of a rotating chopper, or an analyzer in which ultraviolet rays are used as the light or the material to be analyzed is a liquid.

As above described, an analyzer according to the present invention is characterized by having the light source body with focal points at a light source at one end and within a cell at the other end thereof, the curved inner reflective surface of the body being shaped so that scattered light radiated from the light source provided at the one focal point is reflected by the inside surface of the body to the other focal point within the cell. Accordingly, said reflected light is incident upon the cell in addition to light which has not been scattered after radiating from the light source and is directly incident upon the cell. Thus, the light radiated from the light source can be efficiently directed in great quantities upon the cell, so that the detecting sensitivity can be heightened, whereby a highly accurate measurement can be achieved.

Moreover, since a large quantity of light can be directed into the cell even though the cell has a small diameter, the volume of the cell can be reduced, thereby reducing the quantity of fluid required for the measurement. This effect is increased particularly in the case of a fluid-modulation type analyzer.

Further, since an expensive lens and laser light source are not required, this type analyzer can be inexpensively constructed.

What is claimed is:

1. A fluid analyzer comprising:
   a light source;
   a cell for receiving fluid to be analyzed and reference fluid and positioned to receive light from the light source;
   a detector positioned for receiving an output from said cell; and
   a light source body having inner reflective walls with a curved profile in the direction extending between said light source and said cell for forming a first focal point at one end thereof and a second focal point at the other end thereof, said light source being positioned in said light source body substantially coincident with said first focal point, and the other end of said light source body extending around the end of said cell which is toward said light source and with said second focal point within said cell, said curved profile having a shape for reflecting light scattered from said light source only one time into said cell.

2. A fluid analyzer as claimed in claim 1 in which the cross-sectional profile of said light source body is oval.

3. A fluid analyzer as claimed in claim 1 in which the cross-sectional profile of said light source body is constituted by two hyperbolic curves having the respective outer ends connected to each other.

4. A fluid analyzer as claimed in claim 1 in which the cross-sectional profile of said light source body is constituted by two parabolas having the respective outer ends connected to each other.

5. A fluid analyzer as claimed in claim 1 constituted by a hyperbolic curve and a parabolic curve having the respective outer ends connected to each other.

* * * * *